United States Patent
Alauddin et al.

(10) Patent No.: US 10,603,137 B2
(45) Date of Patent: Mar. 31, 2020

(54) ORTHODONTIC ALIGNERS AND DEVICES, METHODS, SYSTEMS, AND COMPUTER PROGRAMS UTILIZING SAME

(71) Applicant: Ormco Corporation, Orange, CA (US)

(72) Inventors: Sammel Shahrier Alauddin, Rancho Cucamonga, CA (US); Jessica E. Grande, Chino, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 15/250,448

(22) Filed: Aug. 29, 2016

(65) Prior Publication Data
US 2017/0056131 A1  Mar. 2, 2017

Related U.S. Application Data

(60) Provisional application No. 62/212,103, filed on Aug. 31, 2015.

(51) Int. Cl.
*A61C 7/08* (2006.01)
*A61C 7/00* (2006.01)
(Continued)

(52) U.S. Cl.
CPC .............. *A61C 7/08* (2013.01); *A61B 5/0022* (2013.01); *A61B 5/682* (2013.01); *A61B 5/742* (2013.01);
(Continued)

(58) Field of Classification Search
CPC ........... A61C 7/08; A61C 7/002; A61C 19/04; A61C 19/063; A61C 2204/085;
(Continued)

(56) References Cited

U.S. PATENT DOCUMENTS 5,078,153 A * 1/1992 Nordlander .......... A61B 5/0002
128/905
5,693,886 A * 12/1997 Seimiya .................. G01L 1/142
73/718

(Continued)

FOREIGN PATENT DOCUMENTS

| CN | 104127253 A | 11/2014 |
| WO | 2012064684 A2 | 5/2012 |
| WO | 2016139271 A1 | 9/2016 |

OTHER PUBLICATIONS

C.T. Drake, S.P. McGorray, C. Dolce, M. Nair, T.T. Wheeler, Orthodontic Tooth Movement with Clear Aligners,: ISRN Dentistry, vol. 2012, Article ID 657973, 7 pages.
(Continued)

*Primary Examiner* — Sean M Michalski
*Assistant Examiner* — Shannel N Wright
(74) *Attorney, Agent, or Firm* — Wood Herron & Evans LLP

(57) ABSTRACT

Devices, methods, systems, and computer program products for quantifying the amount of pressure exerted on a tooth or a set of teeth by an aligner. The quantification may be facilitated by a sensor disposed in the aligner and the sensor may be configured to generate an output signal signifying the amount of pressure in response to receiving an input signal. The input signal may be generated by a detection instrument or a computing device. The amount of pressure may be stored in a treatment tracking software and/or treatment tracking database for review and consideration by a treatment professional. The treatment professional may thereafter make decisions about the orthodontic treatment based on quantified amount of pressure on the tooth or set of teeth.

36 Claims, 8 Drawing Sheets

(51) Int. Cl.
*A61C 19/04* (2006.01)
*A61B 5/00* (2006.01)

(52) U.S. Cl.
CPC ............ *A61B 5/746* (2013.01); *A61B 5/7465* (2013.01); *A61C 7/002* (2013.01); *A61C 19/04* (2013.01); *A61B 2562/0247* (2013.01)

(58) Field of Classification Search
CPC ........ A61C 2204/00–007; A61B 5/682; A61B 5/002; A61B 5/742; A61B 5/746; A61B 5/7465; A61B 2562/0247; A61B 5/6483; A61B 5/1111; A61B 5/1036; A61B 5/224; A61B 5/228; A61B 5/4557; A61B 5/4547; A63B 1/085; G01L 1/14; G01L 1/127; G01L 13/02–028; G01D 5/22–2291; G01D 5/12–40
USPC ............................................. 73/780, 862.626
See application file for complete search history.

(56) References Cited

U.S. PATENT DOCUMENTS

| | | | |
|---|---|---|---|
| 6,386,864 B1 * | 5/2002 | Kuo | A61C 7/00 433/215 |
| 7,147,466 B1 | 12/2006 | Hilliard et al. | |
| 8,919,211 B1 * | 12/2014 | Hanson | G01L 1/146 73/862.626 |
| 2006/0068353 A1 * | 3/2006 | Abolfathi | A61C 7/00 433/6 |
| 2006/0166157 A1 * | 7/2006 | Rahman | A61B 5/4833 433/6 |
| 2007/0065768 A1 * | 3/2007 | Nadav | A61C 7/006 433/6 |
| 2008/0119698 A1 * | 5/2008 | Tricca | A61B 5/0088 600/309 |
| 2009/0074251 A1 * | 3/2009 | Sears | G06T 7/246 382/106 |
| 2009/0286195 A1 * | 11/2009 | Sears | A61C 7/14 433/8 |
| 2010/0036286 A1 * | 2/2010 | Scholz | A61B 5/0002 600/590 |
| 2010/0138025 A1 * | 6/2010 | Morton | A61C 7/00 700/104 |
| 2012/0062245 A1 * | 3/2012 | Bao | H01L 29/84 324/661 |
| 2012/0075241 A1 * | 3/2012 | Bao | H01L 29/84 345/174 |
| 2013/0041244 A1 * | 2/2013 | Woias | A61B 5/0215 600/381 |
| 2013/0234263 A1 * | 9/2013 | Ikehashi | B81B 3/0018 257/415 |
| 2014/0134561 A1 * | 5/2014 | Smith | A61C 19/00 433/6 |
| 2014/0257051 A1 * | 9/2014 | Cam | A61B 5/682 600/301 |
| 2014/0296688 A1 * | 10/2014 | Lam | A61B 3/107 600/399 |
| 2014/0329192 A1 * | 11/2014 | Kaskoun | A61C 19/063 433/6 |
| 2014/0350348 A1 * | 11/2014 | Tee | A61B 5/0002 600/300 |
| 2015/0305671 A1 * | 10/2015 | Yoon | A61B 5/01 600/301 |
| 2016/0256240 A1 * | 9/2016 | Shivapuja | A61C 7/08 |
| 2017/0031491 A1 * | 2/2017 | Bao | G06F 3/0416 |
| 2017/0251954 A1 * | 9/2017 | Lotan | A61C 1/052 |
| 2017/0252140 A1 * | 9/2017 | Murphy | A61C 19/04 |

OTHER PUBLICATIONS

A.M. Bollen, G. Huang, G. King, P. Hujoel, T. Ma, "Activation time and material stiffness of sequential removable orthodontic appliances. Part 1: ability to complete treatment," American Journal of Orthodontics and Dentofacial Orthopedics, vol. 124, No. 5, pp. 496-501, 2003.

N.D. Kravitz, B. Kusnoto, E. BeGole, A. Obrez, B. Agran, "How well does Invisalign work? A prospective clinical study evaluating the efficacy of tooth movement with Invisalign," American Journal of Orthodontics and Dentofacial Orthopedics, vol. 135, No. 1, pp. 27-35, 2009.

T. Duong, E. Kuo, "Finishing with Invisalign," Progress in Orthodontics, vol. 7, No. 1, pp. 44-55, 2006.

D.J. Lipomi, M. Vosgueritchian, B.C-K. Tee, S.L. Hellstrom, J.A. Lee, C.H. Fox, Z. Bao, "Skin-Like Sensors of Pressure and Strain Enabled by Transparent, Elastic Films of Carbon Nanotubes," Nature Nanotechnology, vol. 6, pp. 788-792, 2011.

European Patent Office, European Search Report in EP Application No. 16186638.9, dated Jan. 30, 2017.

European Patent Office, Official Letter in corresponding EP Patent Application No. 16186638.9 dated Jun. 14, 2019.

* cited by examiner

ORTHODONTIC ALIGNERS AND DEVICES, METHODS, SYSTEMS, AND COMPUTER PROGRAMS UTILIZING SAME

CROSS REFERENCE TO RELATED APPLICATIONS

This application claims priority to U.S. Provisional Patent Application Ser. No. 62/212,103 filed Aug. 31, 2015, the disclosure of which is incorporated by reference herein in its entirety.

TECHNICAL FIELD

The invention relates generally to orthodontic aligners, and in particular, to devices, methods, systems, and computer program products for quantifying the amount of force being applied to a tooth during orthodontic treatment of the tooth with an aligner. The invention further generally relates to using the collected information to provide a more efficient orthodontic experience for the patient.

BACKGROUND

Aligners are a series of tight-fitting custom-made retainers that slip over the teeth. Orthodontic aligners are typically used for patients who have mild or moderately crowded teeth, or have minor spacing issues. Patients who have severe crowding or spacing problems, a severe under-bite, a severe over-bite, or a cross-bite, may need more complex treatment. Once a dentist, orthodontist, or treatment professional decides how to correct the patient's bite, a plan is made for moving the teeth from the starting position to the final proposed position. A patient is fitted for several versions of aligners that make slight adjustments to move the teeth over the treatment time. Aligners are typically formed from a clear plastic or acrylic material to fit tightly over the teeth, but can be removed for eating, brushing, and flossing. Patients typically receive a new aligner every few weeks to continue moving the teeth into the desired position. Treatment time with an aligner is based on how much the teeth need to be moved or rotated. The more a bite is off or the more crooked the teeth, the longer the treatment. Treatment usually takes between ten and twenty-four months.

While aligners are gaining in popularity, they remain a relatively new technology in the field of orthodontia. As such, there is unfortunately a limited amount of research on orthodontic tooth movement using aligners. Most of the literature consists of case reports, editorials, blogs, or articles written by authors who may have a bias. There are very few evidence-based attempts to describe the type of tooth movement resulting from treatment with aligners. While there is no consensus in the field directed to an interpretation of the results of these studies, conventional thinking suggests that the movement is mostly uncontrolled tipping, with the center of rotation located between the center of resistance and the apex of the tooth.

FIGS. 1A and 1B illustrate a movement of a tooth in accordance with the conventional understanding of aligners in the field. As shown in FIGS. 1A and 1B, a tooth 2 is disposed in a gum tissue 4 at a first orientation. As a force is applied in the direction of Arrow A, tooth 2 rotates about a center of rotation 6 from the first orientation (FIG. 1A) to a second orientation (FIG. 1B). The rotation generally follows the path of Arrow B in FIG. 1B.

The orthodontic field is uncertain regarding what magnitude of sustained force is needed to move a typical tooth and what length of time the given force should be applied. Aligners are generally believed to move teeth 1 millimeter per month, without a clear understanding of whether this is optimal, efficient, or even correct across all patients. The industry standard is generally to apply a particular aligner to a set of teeth for two weeks. However, there is no evidence to suggest two weeks is the correct amount of time. Many practitioners believe the two week standard is heavily influenced by the material weaknesses of the first generation aligners, where the aligner would stretch and lose rigidity and force starting at about two weeks. However, more modern aligners do not suffer from similar losses of rigidity or inconsistent forces over time.

As shown in FIG. 2, the best results in tooth velocity or tracking are achieved when the periodontal pressure is in an optimal range 8. The optimal range 8 is known in the field and is about 1.5 N/cm$^2$ to 2.6 N/cm$^2$ of pressure on a given tooth. The optimal range 8 correlates to the amount of pressure needed to move a tooth while not harming the tooth, gums, or root in the process due to the applied pressure. If periodontal pressure is too low, the gum and root tissue will not react and the tooth will remain in place. If periodontal pressure is too high, root resorption may occur. Root resorption, is the breakdown or destruction and subsequent loss of the root structure of a tooth. This is caused by living body cells attacking part of the tooth. Severe root resorption is very difficult to treat and often requires the extraction of the tooth. Resorption may occur as a result of trauma, ectopic teeth erupting in the path of the root, chronic inflammation, excessive occlusal loading, or aggressive tumors, cysts, or other growths. However, the most common cause of root resorption in Western society is misapplied orthodontic forces.

Thus, ensuring aligners are within the optimal range 8 illustrated in FIG. 2 is extremely important, as catastrophic loss of a tooth is minimized, while tooth movement is maximized. As such, keeping aligners within the optimal range 8 provides major medical and economic advantages to the patient as well as the orthodontist or treatment professional. Unfortunately, there is a great deal of uncertainty in knowing the amount of force a given aligner is producing on a given tooth. Currently, there is no accurate way of measuring the force of an aligner on a tooth in vivo. Further, while the initial force is unknown, aligner forces may change over time in the oral environment due to deformation of the aligner or as a natural consequence of moving a set of teeth into a more desired position. Still further, the forces exerted on a tooth are complex and do not conform to a standard linear delivery. Thus, modeling or even approximating the force on a tooth from an aligner is extremely complex and there currently exists no accurate way to quantify the amount of force applied to teeth in aligners today.

One of the major drawbacks that may prolong the use of aligners in patients is non-compliance by the patient. In many cases, subjects who begin clear aligner treatment deviate from the programmed progression of aligners and require reevaluation, midcourse correction, and/or use of fixed appliances to achieve treatment goals. Not wearing an aligner as directed for twenty-two hours per day significantly slows the progression of treatment. Some treatment professionals believe that not wearing an aligner for one hour out of the twenty two hours as directed will require an additional twenty four hours of wear time to make up for the one missed hour. Other issues include miscalculation of treatment by the orthodontist or treatment professional, not selecting a good candidate for alignment treatment, and tooth movement stages not going as planned.

As of today, there exists no way to quantify the amount of force being applied to a tooth during aligner treatment. The orthodontist or treatment professional must rely on professional expertise, software, and visual inspection to predict and facilitate the treatment. A better understanding of the mechanics of tooth movement using aligners could lead to more appropriate selection of patients, better sequencing of tooth movement stages, and more efficient treatment. Thus, improved devices, systems, methods, and computer program products for quantifying the amount of force being applied to a tooth during orthodontic treatment of the tooth with an aligner are needed to provide a more efficient orthodontic experience for the patient as well as the orthodontist or treatment professional.

SUMMARY

In an embodiment of the invention, a device is the provided. The device includes an orthodontic aligner adapted to fit a set of teeth. The device further includes a sensor disposed in the aligner and configured to sense a pressure value between the aligner and a tooth in the set of teeth.

In another embodiment of the invention, a method is provided. The method includes sensing, by a sensor disposed in an aligner, a pressure value exerted on a tooth by the aligner. The method further includes actuating the sensor to provide the pressure value.

In another embodiment of the invention, a method is provided. The method includes quantifying a pressure value applied to each tooth in a set of teeth by an orthodontic aligner. The method further includes providing the pressure values for each tooth to a treatment professional associated with the aligner.

In another embodiment, a system for quantifying an amount of pressure exerted on a tooth of a patient during orthodontic treatment of the tooth with an aligner is provided. The system includes a detection instrument configured to actuate a sensor disposed in the aligner and associated with the tooth. Detection instrument is further configured to receive an output signal from the sensor, wherein the output signal signifies the amount of pressure on the tooth. The system further includes a processor and a memory including instructions that, when executed by the processor, cause the system to: receive the amount of pressure from the detection instrument; store the amount of pressure in a treatment tracking database; and display the amount of pressure on a display.

In another embodiment of the invention, a computer program product comprising a non-transitory computer-readable storage medium and instructions stored on the non-transitory computer-readable storage medium is provided. The instructions, when executed by a processor, cause the processor to receive an amount of pressure exerted on a tooth by an orthodontic aligner. The instructions, when executed by the processor, further cause the processor to store the amount of pressure in a treatment tracking database. The instructions, when executed by the processor, further cause the processor display the amount of pressure on a display.

In another embodiment of the invention, an orthodontic aligner is provided. The orthodontic aligner includes a pocket defined by the aligner and adapted to receive a portion of a tooth therein and a sensor disposed in the aligner and proximate the pocket, wherein the sensor is configured to measure a performance variable associated with the aligner.

In yet another embodiment of the invention, a system comprising an aligner is provided, wherein the aligner is adapted to reside in a mouth of a user in vivo. The system further comprises a sensor disposed in the aligner and configured to measure a performance value of the aligner in vivo and a detection instrument configured to collect the performance value from the sensor in vivo.

BRIEF DESCRIPTION OF THE SEVERAL VIEWS OF THE DRAWINGS

The accompanying drawings, that are incorporated in and constitute a part of this specification, illustrate various embodiments of the invention and, together with the general description of the invention given above, and the detailed description of the embodiments given below, serve to explain the embodiments of the invention.

DETAILED DESCRIPTION

Figure 1A:
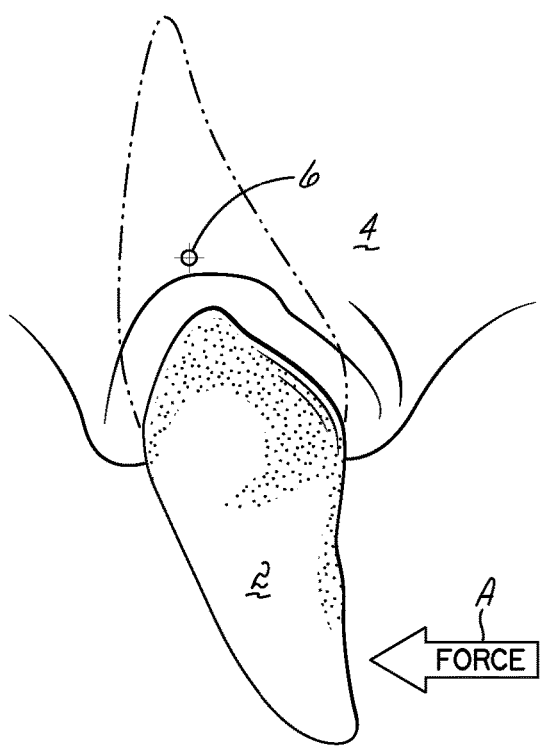
FIG. 1A is a side elevational view of a tooth in a first position.
Figure 1B:
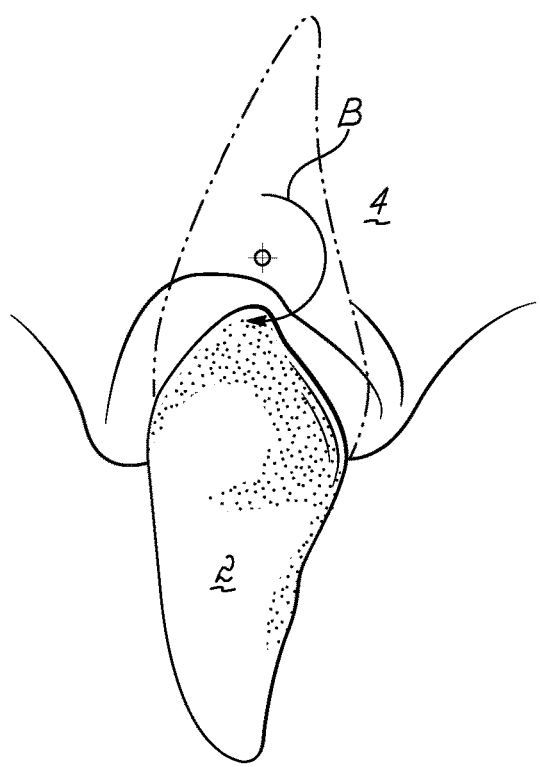
FIG. 1B is a side elevational view of the tooth of FIG. 1A rotated into a second position.
Figure 2:
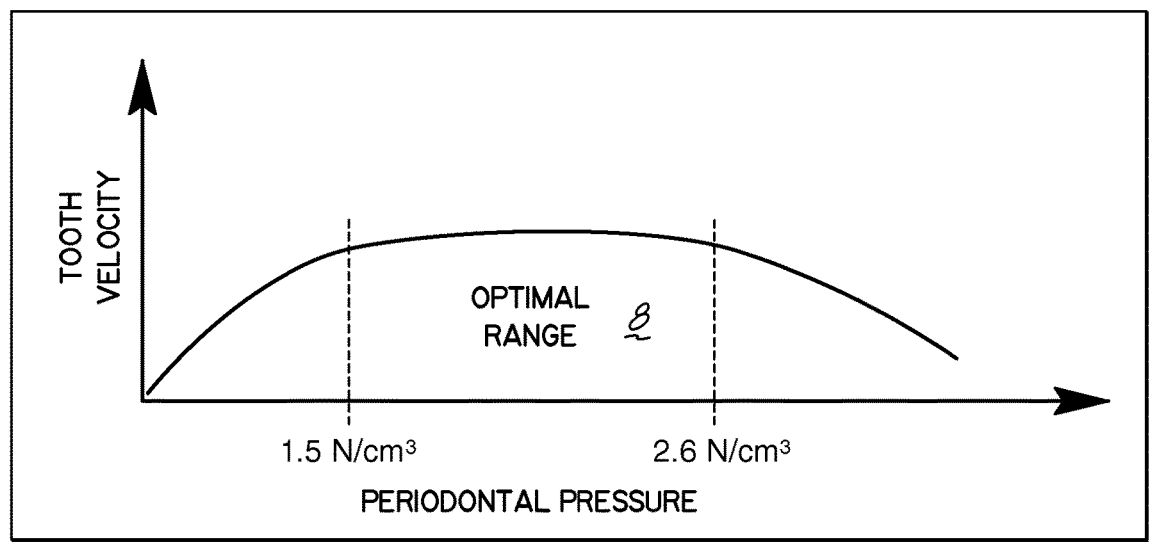
FIG. 2 is a diagrammatic view of tooth velocity relative to periodontal pressure.

Embodiments of the invention are directed to devices, systems, methods, and computer program products for quantifying the amount of force being applied to a tooth during orthodontic treatment of the tooth with an aligner and thereafter using the collected information to provide a more efficient orthodontic experience for the patient. Embodiments of the invention may be implemented by an aligner having a plurality of sensors disposed therein, with each sensor positioned to align with a particular tooth of the patient. The sensor may be disposed or encapsulated between a first layer and a second layer of the aligner. The sensor may include a deforming layer disposed between two inductive electrodes, such that an output signal emitted by the sensor in response to receiving an input signal varies in accordance with the relative space between the two inductive electrodes. Instruments may be provided to sense the output signals from each sensor and derive a pressure reading based on the frequency of the received signal, as the frequency varies depending on the pressure applied to the sensor.

Embodiments of the invention may be implemented by a detection instrument, whereby the detection instrument is configured to emit input signals to resonate the two inductive electrodes of the sensors such that an output signal is emitted by the sensors in return. The detection instrument thereafter collects the output signals emitted by the sensors and passes the pressure information on to a treatment tracking software application. The treatment tracking software application may thereafter be used by the orthodontist or treatment professional in treating the patient.

In an embodiment of the invention, the detection instrument interacts with the sensors in an office setting, such as the orthodontist's office or clinic. In another embodiment of the invention, the detection instrument is provided to the patient for use in a home environment and the detection instrument is configured to pass the pressure information over a network such as the Internet to the treatment tracking software application residing in the orthodontist's office or clinic. Thereafter, the orthodontist or treatment professional may review the pressure information without the patient in the office, saving time and costs for both the patient and the orthodontist. In some scenarios, the detection instrument may not be configured to pass pressure information directly from the patient's home to the orthodontist's office. As such, the patient may also be provided with a communication device for facilitating the transfer of information from the detection instrument to the treatment tracking software application. For example, the communication device may include a cellular network interface card or another mechanism for passing information between the detection instrument and the treatment tracking software. The communication device may comprise the patient's own computing device, such as a smartphone or a tablet computer, with an application installed thereon to facilitate communication between the patient's computing device and the treatment tracking software application. In an embodiment of the invention, the detection instrument may be the patient's own computing device with an application installed thereon. In this embodiment, the particular signal generating and receiving features of the underlying personal computing device are utilized, such as near field communication (NFC) technology or similar.

The treatment tracking software application may be configured to alert the orthodontist or treatment professional when a given parameter is met or exceeded, such as when a particular pressure exerted on a tooth is beyond a set pressure threshold. Notifications may be in the form of email, text message, pre-recorded phone call, fax, a notification message within the treatment tracking software application, or any other mechanism for alerting the orthodontist or treatment professional that a given parameter is met. For example, if a particular sensor indicates the pressure on the associated tooth is greater than a given pressure threshold, the treatment tracking software may be configured to generate an alert in the form of an email to the orthodontist with the patient's name, the tooth at issue, and the pressure reading for the tooth at issue. Thereafter the orthodontist may review the email and the patient's records and determine whether to schedule an appointment with the patient.

The treatment tracking software application may reside on a treatment tracking server having an interface provided on a display. The treatment tracking software application may condense or synthesize the collected raw pressure data into various charts or convenient metrics for use by the orthodontist or treatment professional. For example, the most current pressure reading for each tooth may be displayed along side of the target pressure and the overall average pressure exerted on the tooth through use of the particular aligner. Through use of the sensor readings of the aligner and the treatment tracking software application, the overall treatment of the patient may be enhanced as the orthodontist or treatment professional is provided a quantified measurement of the pressures acting on the patient's teeth. As such, the orthodontist may determine the shortest and quickest path to completing the treatment while minimizing errors and scheduling only necessary in-office time with the patient.

Figure 3:
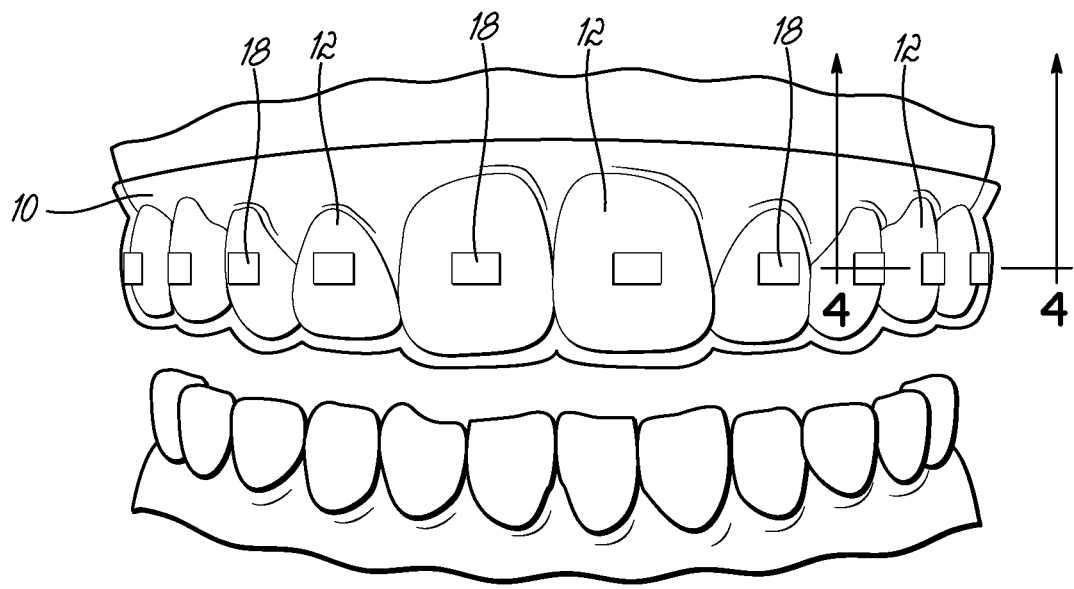
FIG. 3 is a front perspective view of an exemplary aligner disposed on a set of teeth.
Figure 4:
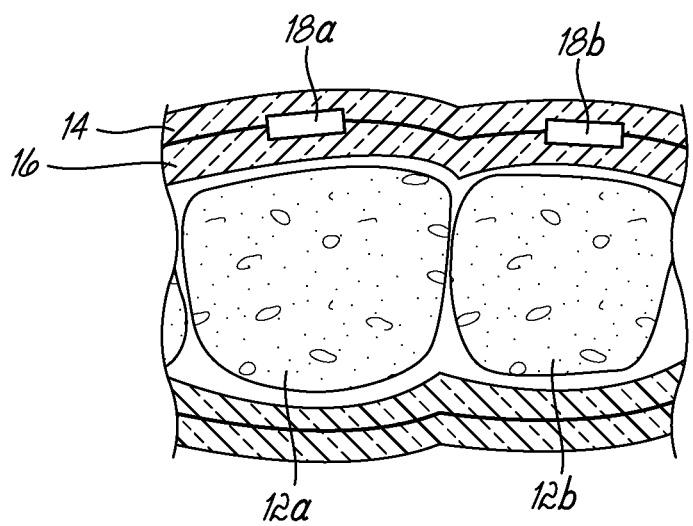
FIG. 4 is a cross-sectional view of the exemplary aligner and teeth taken along line 4-4 of FIG. 3.

Referring now to FIGS. 3 and 4, an aligner in accordance with an embodiment of the invention is illustrated as aligner 10. Aligner 10 may be configured and customized to fit onto a set of teeth 12 and may include two layers, an outer layer 14 and an inner layer 16. A plurality of sensors 18 are disposed between outer layer 14 and inner layer 16 and held firmly therebetween. The configuration of aligner 10 and the placement of each sensor 18 therein may position each sensor 18 adjacent to a corresponding tooth 12. To illustrate, as shown in FIG. 4, sensor 18A is generally aligned to correspond with tooth 12A, while sensor 18B is generally aligned to correspond with tooth 12B. Inasmuch as each sensor 18 is disposed in aligner 10 and aligner 10 is configured to press firmly against the set of teeth 12, each sensor 18 is configured to measure the pressure and/or force with which aligner 10 exerts against the corresponding tooth 12. While the sensors are described in relation to a corresponding tooth, sensors do not necessarily have to align with a particular tooth. By way of further example, a plurality of sensors may be arranged in an array, and the array may correspond to a certain area in the patient's mouth.

Figure 5:
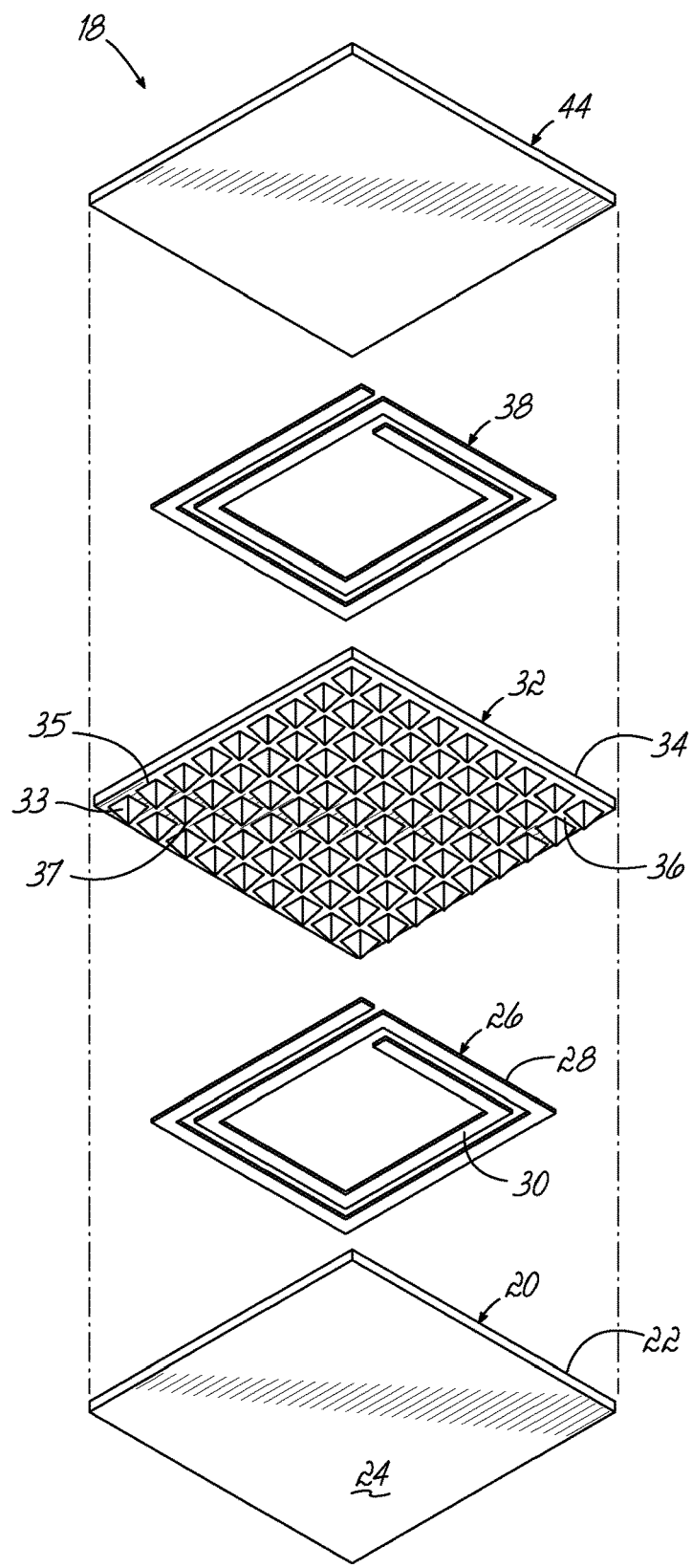
FIG. 5 is an exploded perspective view of an exemplary sensor.

As shown in FIG. 5, sensor 18 may be constructed using several layers of flexible substrates. In an embodiment of the invention, sensor 18 includes five layers, a first layer, a second layer, a third layer, a fourth layer, and a fifth layer. First layer, referred to as a bottom film 20, includes a top surface 22 and a bottom surface 24. Bottom film 20 may be formed of a clear material and/or a material having conductive properties. Second layer, referred to as a first inductive electrode or a bottom inductive electrode 26, includes a top surface 28 and a bottom surface 30. Bottom inductive electrode 26 may be formed of a copper material and may be in a coiled shape.

Third layer 32 of sensor 18, referred to as a deforming layer 32, includes a top surface 34 and a bottom surface 36. Deforming layer 32 may include a plurality of deforming elements 33. In an embodiment of the invention, deforming elements 33 may be formed in a pyramid shape and made of a rubber material. In another embodiment of the invention, deforming elements 33 may be carbon nanotubes or any other mechanism for adjustably and deformably residing between the second layer and the fourth layer of sensor 18. In the embodiment shown in FIG. 3, each deforming element 33 includes a base 35 secured to bottom surface 36 of deforming layer 32. Further, each deforming element 33 extends downwardly towards top surface 28 of second layer 26, terminating in an apex 37. Given the pyramid shape of the deforming elements 33, when pressure is applied to sensor 18, each deforming element 33 may compress or distort in response to the applied pressure. It will be appreciated that the deforming elements 33 may be formed in other shapes, such as cylinders, extruded hexagons, and cubes. Furthermore, the shape of the deforming layer 33 may influence the sensitivity of the presser sensors due to the change in capacitance.

Fourth layer, referred to as a second inductive electrode or a top inductive electrode 38, includes a top surface 40 and a bottom surface 42. Similar to bottom inductive electrode 26, top inductive electrode 38 may also be formed of a copper material and/or formed in a coiled shape. Finally, fifth layer, referred to as a top film 44, includes a top surface 46 and a bottom surface 48. Similar to bottom film 20, top film 44 may be formed of a clear material and/or a material having conductive properties.

The sensors 18 may be positioned with respect to a corresponding tooth or with respect to an array of sensors that corresponds to an area in the patient's mouth in multiple ways. By way of example only and not limitation, one placement approach utilizes computer algorithms that are capable of texture mapping techniques and that can establish positional mapping between a thermoformed aligner and an un-thermoformed plastic disk from which the aligner is manufactured. By this technique, the desired positions of the sensors in the aligner are traced back to a corresponding position in a un-thermoformed plastic disc. In this prediction approach, a three-dimensional surface model of a thermoformed aligner may be flattened onto a planar parametric domain, which may correspond to a flat plastic disk. In one embodiment, the prediction approach includes keeping the amount of distortion in the flattening process inversely proportional to the amount of physical stretching of the plastic material during forming process.

By way of further example and not limitation, another approach may include a measurement approach in which a marked ruler disk, for example with polar coordinates, may be used to position the sensors at their desired locations in the aligner. In one embodiment, the polar coordinated disk may be marked with a laser or ink. The marked disk is then thermoformed into the desired aligner. Based on the markings, points on the aligner are then measured to identify the tooth surface where the sensors will be positioned. An automated or manual system may then place the sensor along a marked thermoplastic disk in the desired location. Alternatively, a marked disk can also be used to form the aligner if the markings are removable. Removal is believed to be necessary for aesthetic purposes. By way of example only, inks that are water-soluble or that evaporator upon exposure to heat or light may be used to mark the thermoplastic disk. Once the aligner is manufactured, the markings may be removed.

According to either of the exemplary methods of placement of the sensors, once the sensors are placed in the desired positions on one or both of the outer layer 14 and the inner layer 16, the layers 14, 16 may be cold laminated to adhere the sensors 18 to one or both of the layers 14, 16 and hold them in their desired positions. Following cold-lamination or simultaneously with lamination, the assembled layers 14, 16 and sensors 18 may be thermoformed into the desired aligner while fully encapsulating the sensors 18.

Alternatively, in one embodiment, the sensors 18 may be adhered to an already formed aligner and then hermetically sealed to that aligner with another layer. For example, this layer may be added by ultrasonic welding a thermoplastic layer to the aligner or by placing polymer coating over the aligner and sensors. This alternative embodiment may be advantageous because the sensors are not stretched or significantly stressed subsequent to positioning the sensors on the formed aligner.

An electromagnetic signal, such as a radio signal, may be emitted towards bottom inductive electrode 26 and top inductive electrode 38, which in turn may resonate and output a return electromagnetic signal having a particular frequency based on the distance between bottom inductive electrode 26 and top inductive electrode 38. Inasmuch as bottom inductive electrode 26 and top inductive electrode 38 are spaced apart and separated by deforming layer 32, as pressure is applied to sensor 18, deforming layer 32 distorts and changes the distance between bottom inductive electrode 26 and top inductive electrode 38. In turn, the resonating of the applied signal varies depending on the distance between the two inductive electrodes and therefore the frequency of the output signal changes and may be measured by an appropriate instrument. Thus, by correlating the deformation properties of sensor 18 and the instrument, one may passively obtain pressure information from sensor 18 by exciting the two inductive electrodes with an input signal.

Figure 6A:
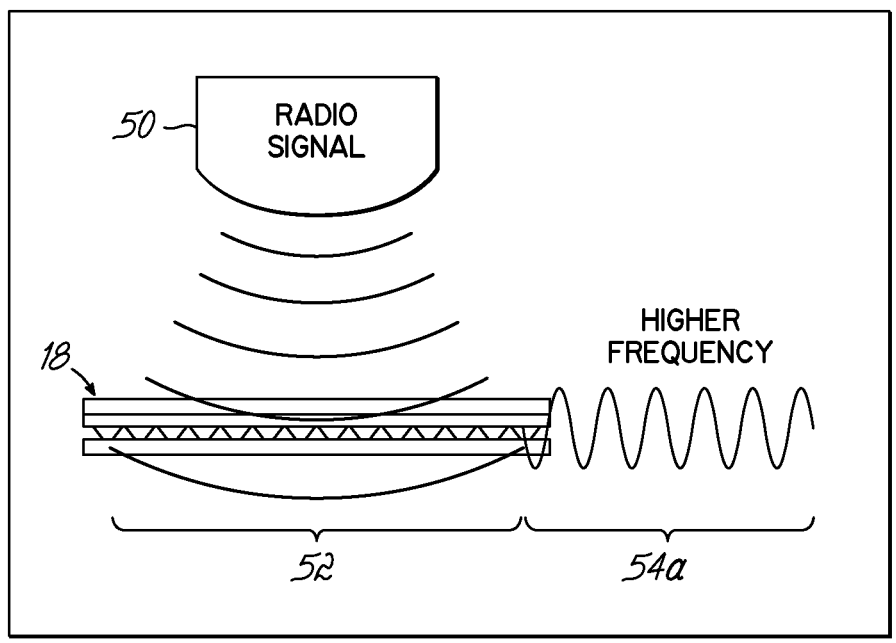
FIG. 6A is a side cut-away view of an exemplary sensor under a first pressure.
Figure 6B:
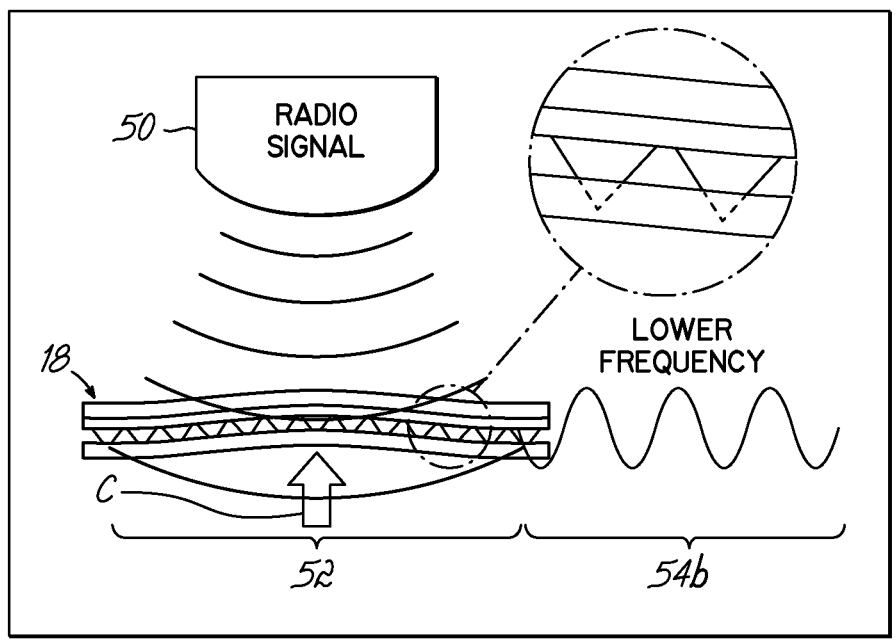
FIG. 6B is a side cut-away view of the exemplary sensor under a second pressure.

As shown in FIGS. 6A and 6B a radio signal source 50 may emit an input signal 52 in the direction of sensor 18 and in response, sensor 18 may emit an output signal 54 having a particular frequency or set of measurable characteristics. The particular output signal 54 emitted by sensor 18 is a function of the distance between bottom inductive electrode 26 and top inductive electrode 38. As shown in FIG. 6A, sensor 18 is in a default or non-deformed state and generates an output signal 54A in response to receiving input signals 52. As shown in FIG. 6B, sensor 18 is in a deformed state and generates an output signal 54B in response to receiving input signals 52. Output signal 54B is lower in frequency with respect to output signal 54A, as pressure in the direction of Arrow C compresses the deforming elements 33 of deforming layer 32. This deformation decreases the distance between bottom inductive electrode 26 and top inductive electrode 38. This decreased distance between bottom inductive electrode 26 and top inductive electrode 38 results in a resonate output signal 54B having a lower frequency in response to receiving input signal 52. Output signals emitted from sensor 18, for example output signal 54A and output signal 54B, are emitted in a calibrated manner and may be compared with an array of resonance frequencies to correlate the precise pressure being applied on sensor 18, as the output signal 54 is a function of the distance between bottom inductive electrode 26 and top inductive electrode 38.

Figure 7:
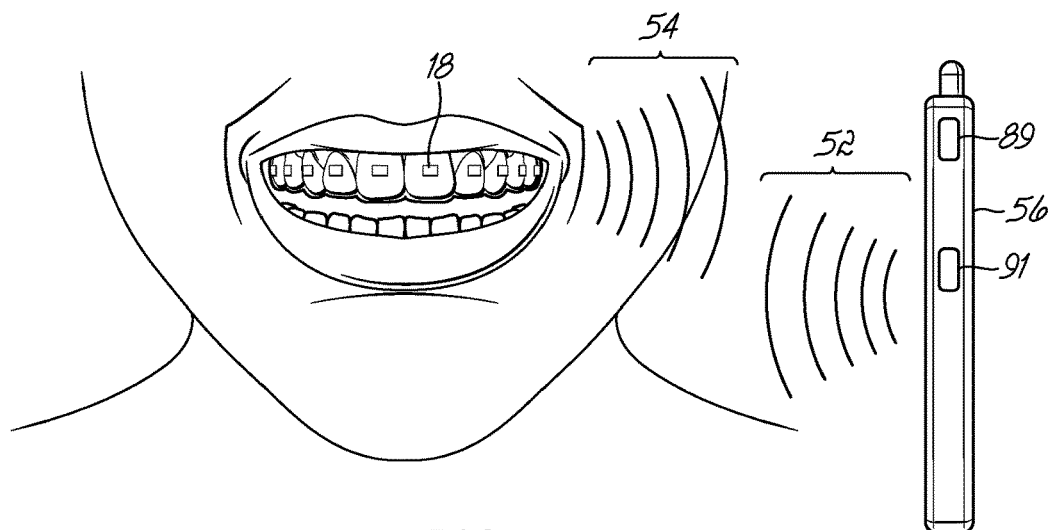
FIG. 7 is a front perspective view of a patient and an exemplary detection instrument.

As shown in FIGS. 3, 4, and 7, in addition to having high resolution pressure sensing capability, each sensor 18 may include the ability to flex, bend and turn to wrap around non-planar surfaces, and integrate with collapsible, stretchable, and mechanically robust materials without wrinkling. These properties are important in order derive detailed tracking information regarding where each tooth 12 is moving and the pressure being applied thereon.

As shown in FIG. 7, a detection instrument 56 may be used to generate input signals 52 and collect the emitted output signals 54 in return. Detection instrument 56 is placed in proximity to aligner 10 while the aligner 10 is disposed on the set of teeth 12 and thus sensing the pressure between aligner 10 and teeth 12. Once in proximity of aligner 10, detection instrument 56 emits input signals 52 and collects output signals 54. Thereafter, detection instrument 56 may store the collected input signals 52 for later retrieval by another component or the detection instrument 56 may generate readings or feedback on an output display (not shown), such as a light emitting diode (LED) screen on detection instrument 56. Alternatively, detection instrument 56 may provide the measured output signals 54 to another component in real time, either through a directed wired connection to the component or wirelessly through a wireless connection. Detection instrument 56 may be a handheld device, either battery powered or directly connectable to a power source via a wire (not shown).

Figure 8:
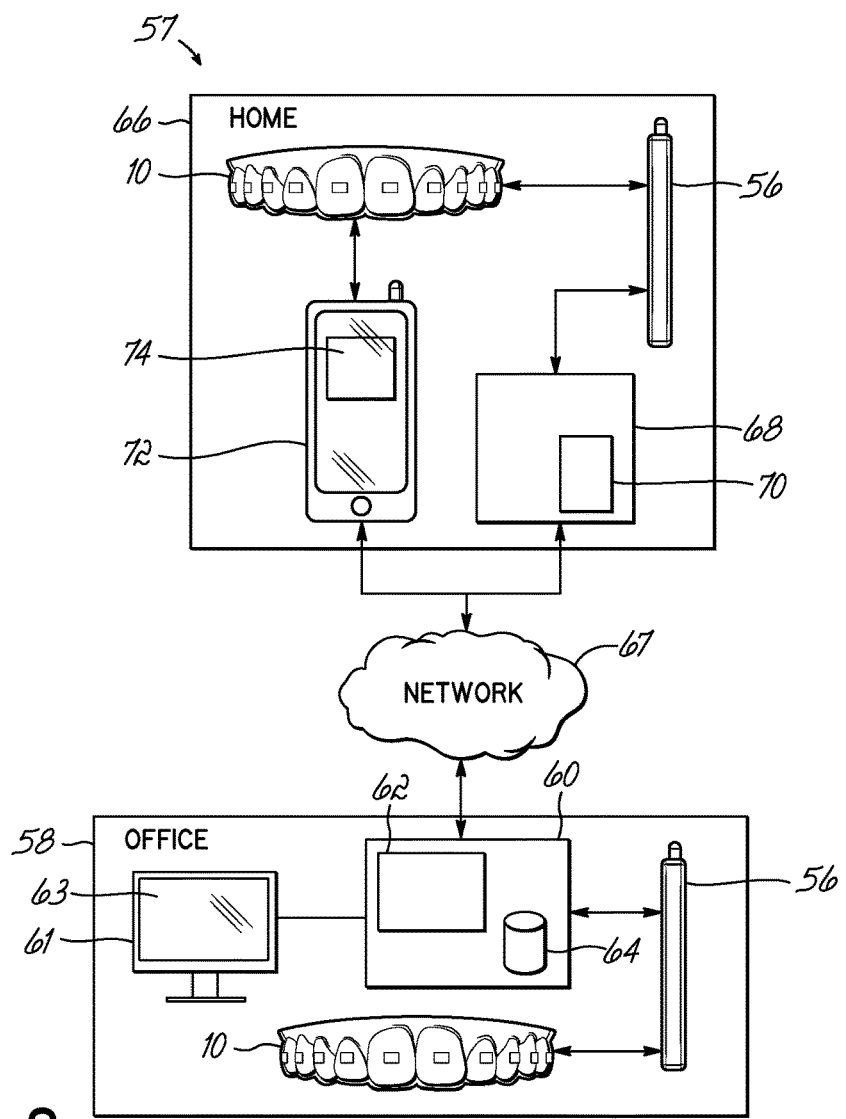
FIG. 8 is a diagrammatic view of an exemplary operating environment including a home setting in communication with an office setting via a network.

FIG. 8 illustrates an exemplary operating environment 57 of aligner 10 where detection instrument 56 may be used in an office 58, such as an orthodontist's office or another office setting where clinical visits occur between a patient wearing aligner 10 and the clinician. In office 58, detection instrument 56 generates input signals 52 that resonate bottom inductive electrode 26 and top inductive electrode 38 for each sensor 18 in aligner 10. The resonation of each sensor 18 generates output signals 54 that are collected by detection instrument 56. Thereafter, detection instrument 56 may be configured to transmit the collected output signals 54 to a treatment tracking server 60, either wirelessly or through a wired connection. The treatment tracking server 60 may include various elements for storing the collected output signals 54 and correlating the output signals 54 with other patient data to track the orthodontic treatment of the patient using the aligner 10. As such, treatment tracking server 60 may include a treatment tracking software application 62 to facilitate tracking the orthodontic pressures and teeth movement for the patient and the aligner 10. Treatment tracking server 60 may also include a treatment tracking database 64 for use in storing the pressure readings acquired by detection instrument 56 and passed to treatment tracking server 60. As such, in an embodiment of the invention, detection instrument 56, treatment tracking server 60, treatment tracking software application 62, and treatment tracking database 64 may communicate and transmit data therebetween to facilitate tracking a patient's orthodontic progress with respect to aligner 10.

Detection instrument 56 may be used outside of office 58, for example, at a patient's home 66. This allows the patient to directly participate in the treatment tracking, independent of clinical office visits. Detection instrument 56 may be loaned to the patient or the patient may purchase a detection instrument 56 as part of the overall cost of the orthodontic procedure. In an embodiment of the invention, the detection instrument 56 includes a buffer sized to hold collected pressure data during the intermittent time between clinical visits with the orthodontist. In this embodiment, the patient brings the detection instrument 56 to office 58 during the scheduled appointment and the orthodontist downloads the pressure data from detection instrument 56 to treatment tracking server 60 in office 58. In another embodiment of the invention, the patient is provided with a communication device 68 for retrieving the collected pressure data from detection instrument 56 and thereafter passing the collected pressure data from home 66 over a network 67 to the office 58, where the data is provided to treatment tracking server 60. Communication device 68 is configured to interface with detection instrument 56 to receive the collected output signals 54 and facilitate passing this information to treatment tracking server 60. Communication device 68 may include a network interface card (NIC) for connecting to network 67 via a wired connection using a protocol such as Ethernet, or may include a cellular network interface card for passing the information over one or more cellular networks to the treatment tracking server 60. Network 67 may include one or more private or public networks (e.g. the Internet) that enable the exchange of data and therefore communication device 68 may include a function for remote access to the treatment tracking server 60 such as a user identifier and/or a password. Communication device 68 may be a tablet computer or a smartphone purposely constructed or customized to interface with detection instrument 56. Alternatively, communication device 68 may comprise an application 70 downloaded to a common off-the-shelf computing device such as a tablet or smartphone. In this embodiment, application 70 may provide the functionality for authenticating and connecting with the treatment tracking server 60.

In lieu of providing the patient with detection instrument 56 and/or communication device 68, the patient may use a personal computing device such as a smartphone 72 with a software application 74 installed. Smartphone 72 may use any technology contained therein for emitting input signals 52 to sensors 18 and collecting output signals 54 back from sensors 18. For example, if smartphone 72 is equipped with the appropriate signal emitting and capturing hardware utilizing signals in the radio frequency range, smartphone 72 may mimic most of the functionality of detection instrument 6. Alternatively, smartphone 72 may use near field communication (NFC) wireless technology. NFC allows smartphone 72 to send information over short distances without the prerequisite of pairing to another device such as Bluetooth® technology. In this embodiment, a NFC chip (not shown) must be connected with the bottom inductive electrode 26, the top inductive electrode 38, or both, requiring extra circuitry. This embodiment allows the patient to utilize an existing computing device to facilitate collecting pressure information from sensors 18. Once smartphone 72 and application 74 collect pressure information, the information is transmitted through network 67 to treatment tracking server 60, as described above with detection instrument 56 and communication device 68.

Figure 9:
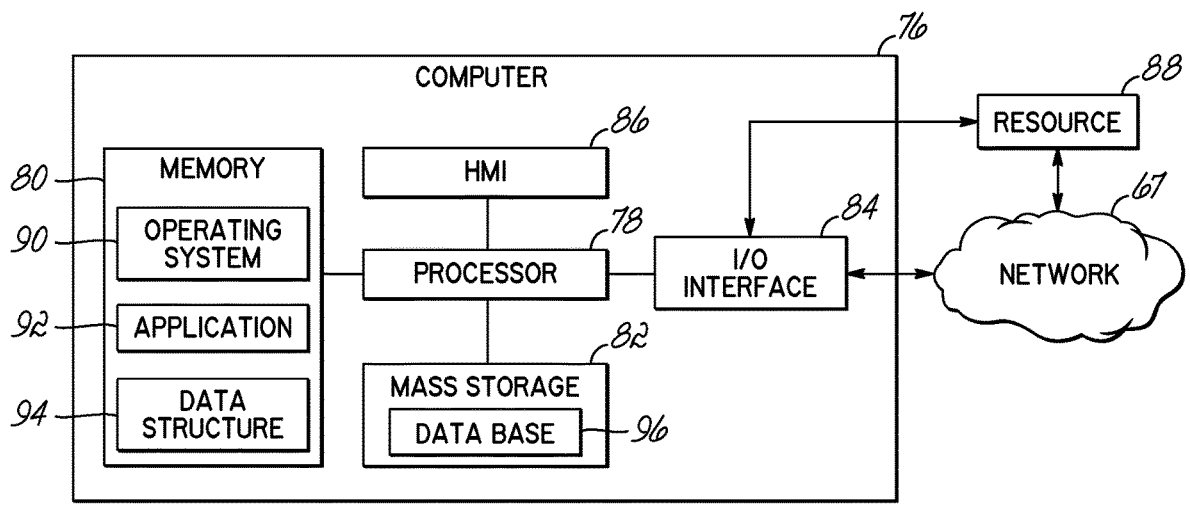
FIG. 9 is a diagrammatic view of an exemplary computer system of FIG. 8.

Referring now to FIG. 9, detection instrument 56, treatment tracking server 60, communication device 68, smartphone 72, and network 67 of operating environment 57 may be implemented on one or more computing devices or systems, such as exemplary computer system 76. The computer system 76 may include a processor 78, a memory 80, a mass storage memory device 82, an input/output (I/O) interface 84, and a Human Machine Interface (HMI) 86. The computer system 76 may also be operatively coupled to one or more external resources 88 via the network 67 or I/O interface 84. External resources may include, but are not limited to, servers, databases, mass storage devices, peripheral devices, cloud-based network services, or any other suitable computer resource that may used by the computer system 76.

The processor 78 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 80. Memory 80 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or any other device capable of storing information. The mass storage memory device 82 may include data storage devices such as a hard drive, optical drive, tape drive, non-volatile solid state device, or any other device capable of storing information.

Processor 78 may operate under the control of an operating system 90 that resides in memory 80. The operating system 90 may manage computer resources so that computer program code embodied as one or more computer software applications, such as an application 92 residing in memory 90, may have instructions executed by the processor 78. Application 92 may comprise application such as treatment tracking software application 62 or software application 74. In an alternative embodiment, the processor 78 may execute application 92 directly, in which case the operating system 90 may be omitted. One or more data structures 94 may also reside in memory 90, and may be used by the processor 78, operating system 90, or application 92 to store or manipulate data.

The I/O interface 84 may provide a machine interface that operatively couples the processor 78 to other devices and systems, such as the network 67 or external resource 88. The application 92 may thereby work cooperatively with the network 67 or external resource 88 by communicating via the I/O interface 84 to provide the various features, functions, applications, processes, or modules comprising embodiments of the invention. The application 92 may also have program code that is executed by one or more external resources 88, or otherwise rely on functions or signals provided by other system or network components external to the computer system 76. Indeed, given the nearly endless hardware and software configurations possible, persons having ordinary skill in the art will understand that embodiments of the invention may include applications that are located externally to the computer system 76, distributed among multiple computers or other external resources 88, or provided by computing resources (hardware and software) that are provided as a service over the network 67, such as a cloud computing service.

The HMI 86 may be operatively coupled to the processor 78 of computer system 76 in a known manner to allow a user to interact directly with the computer system 76. The HMI 86 may include video or alphanumeric displays, a touch screen, a speaker, and any other suitable audio and visual indicators capable of providing data to the user. The HMI 86 may also include input devices and controls such as an alphanumeric keyboard, a pointing device, keypads, push-buttons, control knobs, microphones, etc., capable of accepting commands or input from the user and transmitting the entered input to the processor 78.

A database 96 may reside on the mass storage memory device 82, and may be used to collect and organize data used by the various systems and modules described herein. The database 96 may include data and supporting data structures that store and organize the data. In particular, the database 96 may be arranged with any database organization or structure including, but not limited to, a relational database, a hierarchical database, a network database, or combinations thereof. A database management system in the form of a computer software application executing as instructions on the processor 78 may be used to access the information or data stored in records of the database 96 in response to a query, where a query may be dynamically determined and executed by the operating system 90, other applications 92, or one or more modules. As shown in FIG. 8, in an embodiment of the invention, the database 96 may comprise treatment tracking database 64.

Figure 10:
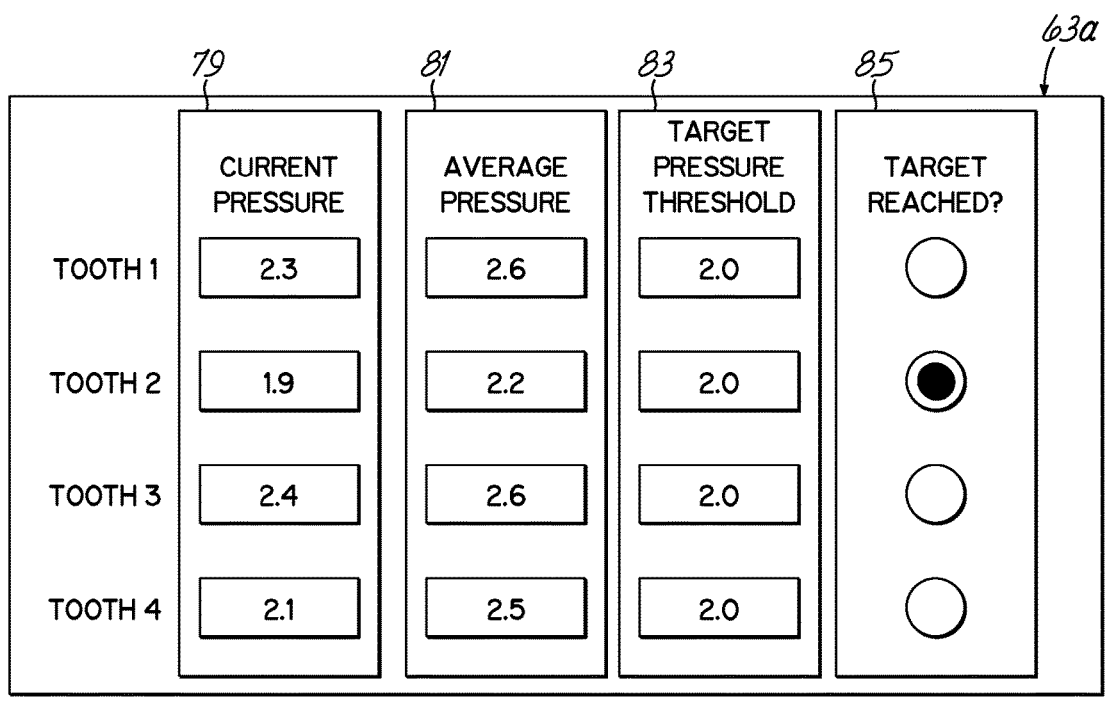
FIG. 10 is a graphical view of an exemplary interface illustrating pressure information with respect to various teeth.
Figure 11:
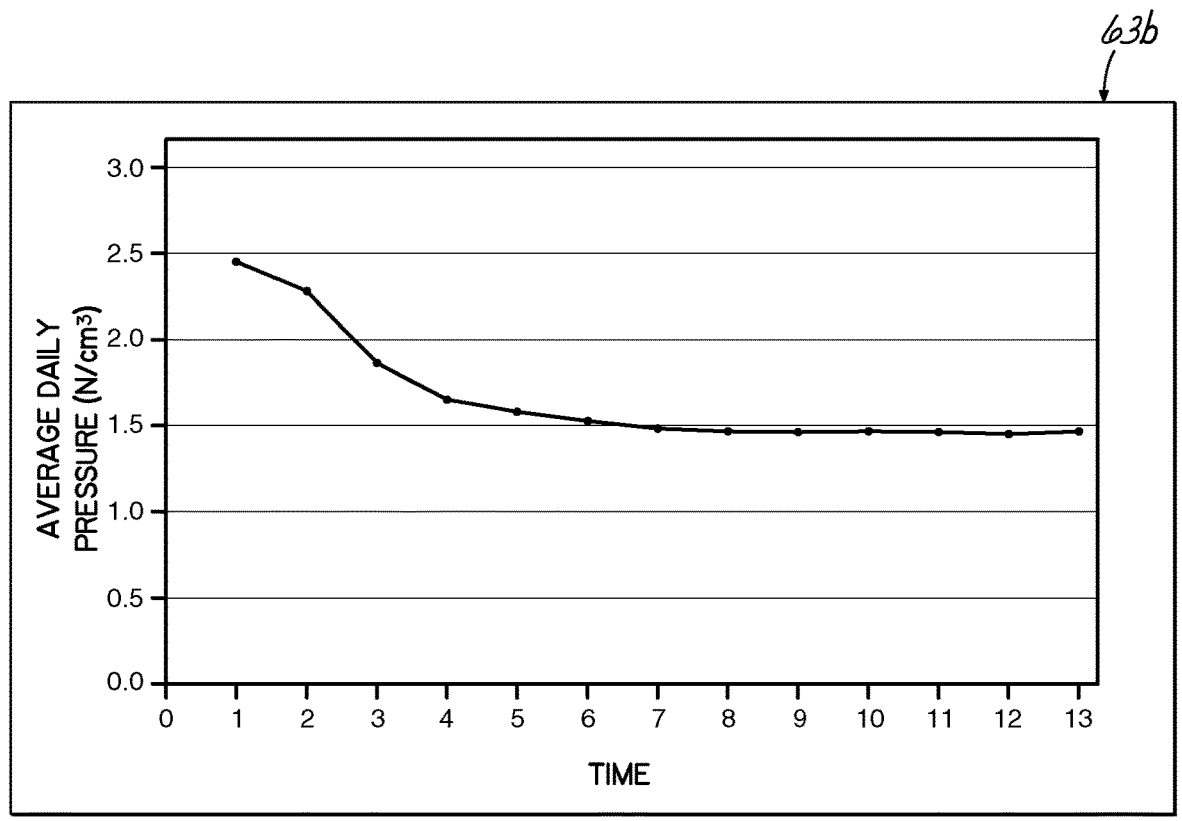
FIG. 11 is a graphical view of an exemplary interface illustrating average daily pressure with respect to time.

With particular reference to FIGS. 10 and 11, interface 63 may provide the orthodontist or treatment professional with condensed or synthesized view of the underlying pressure data collected from aligner 10 and sensors 18 in an easily readable or standardized format. Further, treatment tracking software application 62 may derive additional data from the raw data collected from the patient. For example, as shown in FIG. 10, interface 63A may provide a listing of a current pressure per tooth 79, an average pressure per tooth 81, and a target pressure threshold 82. Current pressure per tooth 79 may indicate the most recent pressure reading collected from the sensor 18 associated with the tooth. Average pressure per tooth 81 may indicate the average pressure with respect to all of the pressure readings collected from the sensor 18 associated with the tooth, or may be a rolling average weighted towards the most recent pressure reading. As a tooth moves in the patient's mouth due to the pressure from aligner 10, the pressure on that tooth will decrease. As such, target pressure threshold 82 may be a threshold set by the orthodontist or treatment professional on a per-tooth basis, or may be a global pressure target to be reached by each tooth.

Interface 63A may also provide an indicator of a target pressure reached per tooth 85 to signify graphically to the user of treatment tracking software application 62 when the particular tooth has moved below the target pressure threshold. A tooth reaching the target pressure threshold may indicate that the tooth is ready for the next aligner 10. Interface 63 may also provide information regarding the position of the tooth in the patient's mouth or any other relevant data that may be beneficial for the orthodontist or treatment professional.

Similarly, interface 63B may provide a graphical representation of the pressure readings from the sensor 18 associated with a particular tooth. As shown in FIG. 11, the pressure readings for each day may be collected and an average for each day generated and graphed along an X-Y plot, where the X-axis indicates the average pressure and the Y-axis indicates the day, relative to the first day the patient started wearing the aligner 10. Thus, an orthodontist or treatment professional can readily observe the relative pressure on the underlying tooth from the aligner 10 over time. The pressures displayed in FIG. 11 illustrate a gentle downward slope and is what an orthodontist would expect to observe if the aligner 10 is working properly. Any anomaly in pressure would be readily recognizable as a spike or dip in the graph and would alert the orthodontist or treatment professional to a problem with an element of aligner 10.

Figure 12:
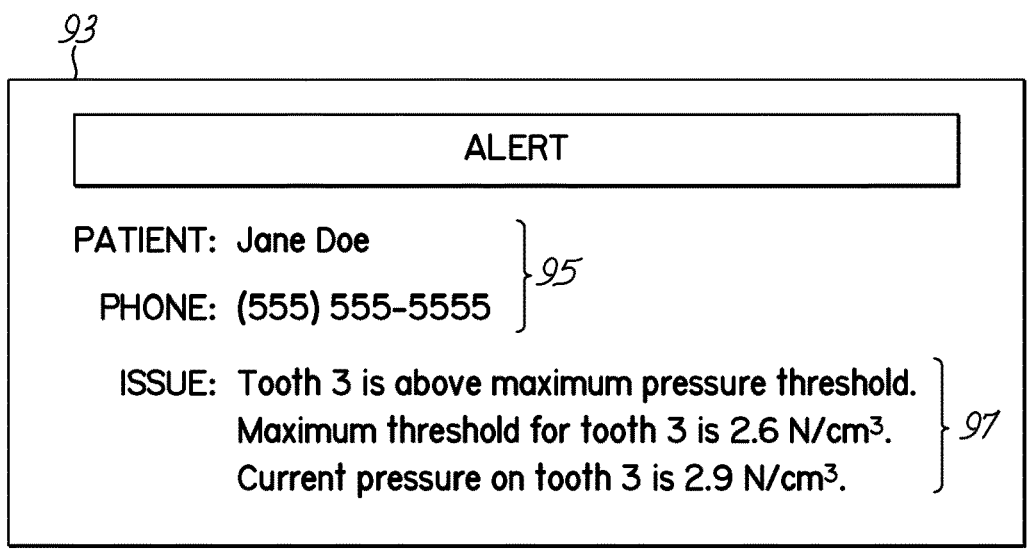
FIG. 12 is a graphical view of an exemplary alert.

As shown in FIG. 12, in an embodiment of the invention, an alert 93 may be generated by treatment tracking software application 62 in response to various triggers or actuation points incorporated into system. For example, when every sensor 18 in a particular aligner 10 are below a set threshold, treatment tracking software application 62 may generate alert 93 to notify the orthodontist that the patent may be ready to be fitted for a new aligner 10. In another example, when a particular sensor 18 provides a pressure reading above a set threshold, treatment tracking software application 62 may generate alert 93 to notify the orthodontist that aligner 10 and/or the patient's teeth may need immediate evaluation to prevent root resorption. Alerts 93 may in the form of an email to the orthodontist or treatment professional, a text message, an internal message available through a notification section of treatment tracking software application 62, or any other mechanism for notifying the orthodontist or treatment professional that a particular threshold is met or any other trigger has been actuated by the collected pressure data. Alerts 93 may include a patient identification 95, such as the patient's name and telephone number. Alerts 93 may also include an issue 97 for informing the recipient of the underlying issue that triggered the particular alert 93. In the particular alert 93 illustrated in FIG. 12, the sensor 18 associated with "tooth 3" generated a pressure reading that was above the maximum set pressure threshold for the tooth. Therefore, such a pressure reading actuated treatment tracking software application 62 and notice 93 was generated in response.

Figure 13:
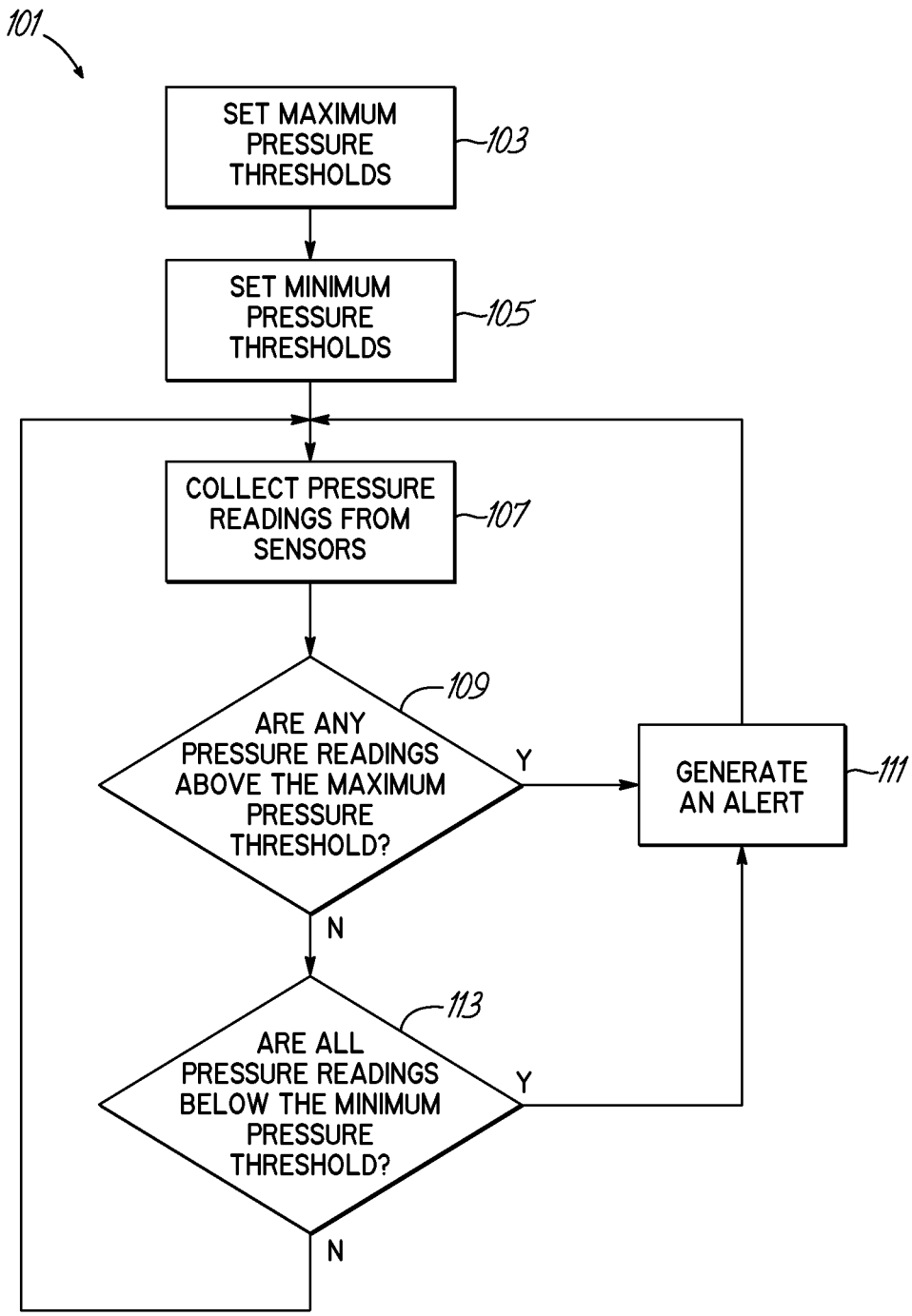
FIG. 13 is a flowchart of an alert generating process that may be performed an embodiment of the invention.

Similarly, FIG. 13 illustrates an embodiment of a process 101 for generating alerts 93. Process 101 begins with a step 103, whereby an orthodontist or treatment professional sets the maximum pressure thresholds for each of the patient's teeth. Alternatively, a global singular maximum threshold may be set for all of the patient's teeth. Thereafter, step 103 proceeds to a step 105. In step 105, an orthodontist or treatment professional sets the minimum pressure thresholds for each of the patient's teeth. Similarly, a global singular minimum threshold may be set for all to of the patient's teeth. Thereafter, step 105 proceeds to a step 107.

In step 107, the pressure readings from each sensor in a particular aligner 10 are collected and step 107 thereafter proceeds to a step 109. In step 109, a determination is made regarding whether any of the collected pressure readings are above the maximum pressure threshold provided in step 103. If it is determined that at least one of the collected pressure readings are above the maximum pressure threshold (the "YES" branch of the decision step), step 107 proceeds to a step 111. If none of the collected pressure readings are above the maximum pressure threshold (the "NO" branch of the decision step), step 107 proceeds to a step 109.

In step 109, a determination is made regarding whether each collected pressure reading is below the associated minimum pressure threshold provided in step 105. If it is determined that each of the collected pressure readings are below their associated minimum pressure thresholds (the "YES" branch of the decision step), step 109 proceeds to step 111. Alternatively, if one or more of the collected pressure readings are not below their associated minimum pressure thresholds (the "NO" branch of the decision step), step 109 proceeds back to step 107.

In step 111, an alert is generated based upon the underlying issue. For example, if a pressure reading is determined to be above the associated maximum pressure threshold, step 111 generates an alert with information relevant to this issue and passes the alert on to the appropriate entity, such as the orthodontist or even the patient, who may then coordinate with the orthodontist how to address the underlying issue. Similarly, if all of the pressure readings are determined to be below their associated minimum pressure thresholds, step 111 generates an alert with this information and transmits the alert to the appropriate entity. Thereafter, the orthodontist may schedule an appointment with the patient for fitting a new aligner for the patient, as the alert notifies the orthodontist that the current aligner has moved the patient's teeth to the correct position relative to that aligner. After the appropriate alert is generated by step 111, step 111 proceeds back to step 107.

Inasmuch as the devices, systems, and methods of the present invention allow the orthodontist to quantify the amount of force being applied to the underlying teeth, several benefits may be realized. For example, the orthodontist may now schedule only necessary appointments as opposed to check in visits where the orthodontist assesses the aligner. Further, given that the treatment is more efficient by precisely determining when the patient is ready for a new aligner, the orthodontist may determine the shortest, quickest path to completing the orthodontic treatment with minimal case reloading. As such, the total treatment time is reduced and the overall operational cost to the orthodontist or treatment professional is reduced.

In operation, an orthodontic treatment professional performs an initial assessment of the patient by reviewing the patient's bite and teeth placement. The treatment professional thereafter determines a treatment plan for the patient prescribing a specific movement of the patient's teeth and bite from an original position into a final position. In accordance with this treatment plan, aligner 10 is constructed to begin moving the patient's teeth from the original position to the final position. As described above, aligner 10 includes sensors 18 positioned proximate each tooth 12 such that each sensor 18 generates pressure information with respect to the underlying tooth 12 associated with the sensor 18. Inasmuch as sensors 18 are encapsulated by aligner 10, sensors 18 are protected from wear and moisture present in the patient's mouth.

In an embodiment of the invention the treatment professional collects pressure data from each sensor 18 in a liner 10 during the initial fitting of aligner 10 in the treatment professional's office 58. This is to ensure that each tooth 12 is receiving pressure from aligner 10 within the appropriate range and to verify the aligner was properly constructed in accordance with the prescribed treatment plan. The treatment professional places detection instrument 56 proximate the patient's teeth and collects pressure values by sending input signals 52 from detection instrument 56 to sensor 18, which in turn generates output signals 54 signifying the pressure on a particular tooth 12 from aligner 10. After the detection instrument 56 collects all of the pressure values from the sensors 18, detection instrument 56 transmits the collected pressure data to treatment tracking software application 62 to be stored in treatment tracking database 64 of treatment tracking server 60.

Each sensor 18 may include two inductive electrodes with a deforming layer disposed therebetween. In the example illustrated in FIG. 5, bottom inductive electrode 26 and top inductive electrode 38 are spaced a distance apart by deforming layer 32. Different amounts of pressure vary the distance between bottom inductive electrode 26 and top inductive electrode 38 by deforming or compressing deforming layer 32 and in turn varying the distance between the two inductive electrodes. When input signal 52 is transmitted into sensor 18, output signal 54 varies in relation to the distance between bottom inductive electric 26 and top inductive electrode 38. This variance provides the pressure value that aligner 10 is exerting on a particular tooth 12.

After the initial fitting of aligner 10 on the patient's teeth, the patient leaves office 58 and returns to the patient's home 66. In an embodiment of the invention, the treatment professional provides the patient with detection instrument 56 as well as communication device 68 for use in the patient's home 66. The treatment professional may prescribe a plan for the patient to collect pressure data from aligner 10 via detection instrument 56 at certain times of the day. For example, the treatment professional may ask the patient to measure the pressure values every 4 hours or once every day. At the appropriate time, the patient places detection instrument 56 proximate aligner 10 to collect pressure data. Detection instrument 56 generates input signals 52 to resonate bottom inductive electrode 26 and top conductive electrode 38 for each sensor 18 within aligner 10. Thereafter, each sensor 18 responds with output signal 54 signifying the pressure value that the aligner 10 is currently exerting on the associated tooth 12. Detection instrument 56 is configured to collect all output signals 54 and transfer this information to communication device 68. Communication device 68, via application 70, thereafter transfers the collected pressure values over network 67 to treatment tracking software application 62 residing on treatment tracking server 60 within office 58. The collected information is stored in treatment tracking database 64 for use by the treatment professional. Alternatively, detection instrument 56 may include functionality to allow direct transfer of pressure values from detection instrument 56 to treatment tracking software application 62 over network 67. In another embodiment of the invention, the patient is not provided with detection instrument 56. Rather, the patient is invited to download software application 74 onto the patient's personal computing device such as smartphone 72. Software application 74 utilizes the built-in features of the patient's smartphone 72, such as NFC communication functionality, to generate input signals 52 and collect output signals 54. Thereafter, smartphone 72 may use additional built-in features such as cellular data transmission capabilities or a connection to the Internet to transfer the collected pressure values over network 67 to treatment tracking software application 62.

The treatment professional may thereafter review the collected pressure values through interface 63 of treatment tracking software application 62. The treatment professional may query treatment tracking database 64 or otherwise manipulate the underlying pressure value data in any way necessary to supervise the treatment of the patient. If any collected pressure values are beyond a preferred range, the treatment professional may contact the patient and proceed addressing the pressure issue as necessary. Treatment tracking software application 62 may be configured to compare the collected pressure values with a maximum threshold and/or a minimum threshold for each tooth 12 and generate an alert if treatment tracking software application 62 determines that a collected pressure value is outside a particular threshold. This alert may be in the form of a text message or an e-mail message communicated to the treatment professional or the patient, notifying the recipient of the pressure issue with aligner 10. Thereafter, treatment professional may take steps to rectify the pressure issue with the patient.

The treatment tracking software application 62 may determine that all of the collected pressure values for each sensor 18 are within a set range for recommending the patient move to the next aligner 10 in the progression of the treatment plan. The treatment tracking software application 62 may passively provide this data to the treatment professional or may generate a notification to the treatment professional informing the recipient that all of the collected pressure values are within a range where moving the patient to the next aligner 10 is appropriate.

In general, the routines executed to implement the embodiments of the invention, whether implemented as part of an operating system or a specific application, component, program, object, module or sequence of instructions, or even a subset thereof, may be referred to herein as "computer program code," or simply "program code." Program code typically comprises computer readable instructions that are resident at various times in various memory and storage devices in a computer and that, when read and executed by one or more processors in a computer, cause that computer to perform the operations necessary to execute operations and/or elements embodying the various aspects of the embodiments of the invention. Computer readable program instructions for carrying out operations of the embodiments of the invention may be, for example, assembly language or either source code or object code written in any combination of one or more programming languages.

Various program code described herein may be identified based upon the application within which it is implemented in specific embodiments of the invention. However, it should be appreciated that any particular program nomenclature that follows is used merely for convenience, and thus the invention should not be limited to use solely in any specific application identified and/or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer readable storage medium having computer readable program instructions thereon for causing a processor to carry out aspects of the embodiments of the invention.

Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. A computer readable storage medium should not be construed as transitory signals per se (e.g., radio waves or other propagating electromagnetic waves, electromagnetic waves propagating through a transmission media such as a waveguide, or electrical signals transmitted through a wire). Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts, sequence diagrams, and/or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, and/or operations specified in the flowcharts, sequence diagrams, and/or block diagrams.

In certain alternative embodiments, the functions, acts, and/or operations specified in the flowcharts, sequence diagrams, and/or block diagrams may be re-ordered, processed serially, and/or processed concurrently consistent with embodiments of the invention. Moreover, any of the flowcharts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A device for use in orthodontic treatment comprising:
    an orthodontic aligner adapted to fit a set of teeth and to apply a periodontal pressure in a range that moves at least one tooth in the set of teeth relative to surrounding gum tissue; and
    a sensor disposed in the orthodontic aligner and configured to sense a decreasing pressure value related to the applied periodontal pressure between the aligner and the at least one tooth in the set of teeth as the at least one tooth is moved by the orthodontic aligner, the sensor comprising a first inductive electrode, a second inductive electrode, and a deforming layer disposed between the first inductive electrode and the second inductive electrode,
    wherein the deforming layer is configured to deform relative to the periodontal pressure.

2. The device of claim 1, wherein the sensor is configured to emit an output radio signal that changes as a function of a distance between the corresponding first and second inductive electrodes.

3. The device of claim 2, wherein the pressure value is based at least in part on the distance between the first inductive electrode and the second inductive electrode.

4. The device of claim 2, further comprising:
    a detection instrument configured to transmit an input signal and collect the output signals from the sensor based on the input signal.

5. The device of claim 4, the detection instrument further comprising:
    a signal transmitter configured to transmit the input signal to the sensor, wherein the input signal resonates the first inductive electrode and second inductive electrode into producing the output signal signifying to the pressure value; and
    a signal receiver configured to receive the output signal.

6. The device of claim 1, wherein the sensor is secured within the aligner.

7. The device of claim 6, wherein the aligner includes a first layer and a second layer, and wherein the sensor is disposed between the first layer and the second layer.

8. The device of claim 1, wherein the sensor is configured to sense a pressure value in a range from 1.5 N/cm$^2$ to 2.6 N/cm$^2$.

9. The device of claim 1, further including a plurality of sensors disposed in the orthodontic aligner at locations so as to position at least one sensor adjacent each tooth in the set of teeth.

10. The device of claim 1 wherein at least one of the inductive electrodes is connected to a near field communication chip.

11. The device of claim 1 wherein the deforming layer includes a plurality of deforming elements, each deforming element including a base and an apex.

12. The device of claim 11 wherein each deforming element is at least one of a pyramid, a cylinder, an extruded hexagon, and a cube.

13. The device of claim 11 wherein each deforming element includes carbon nanotubes.

14. The device of claim 1 wherein the sensor is positioned in the aligner so as to be positioned adjacent the buccal surface or the lingual surface of the at least one tooth and is configured to measure the decreasing pressure value as the at least one tooth is moved by the aligner.

15. A system for quantifying an amount of pressure exerted on a tooth of a patient during orthodontic treatment of the tooth with an orthodontic aligner fitting a set of teeth and applying a periodontal pressure in a range that moves the tooth relative to surrounding gum tissue, the amount of pressure being related to the applied periodontal pressure, the system comprising:
    a detection instrument configured to:
        actuate a sensor disposed in the orthodontic aligner and configured to sense a decreasing pressure value related to the applied periodontal pressure between the aligner and the tooth, the sensor comprising a first inductive electrode, a second inductive electrode, and a deforming layer disposed between the first inductive electrode and the second inductive electrode, wherein the deforming layer is configured to deform relative to the periodontal pressure; and
        receive an output signal from the sensor, wherein the output signal signifies the amount of pressure on the tooth;
    a processor; and
    a memory including instructions that, when executed by the processor, cause the system to:
        receive the amount of pressure from the detection instrument;
        store the amount of pressure in a treatment tracking database; and
        display the amount of pressure on a display.

16. The system of claim 15 further including instructions that, when executed by the processor, cause the system to:
    store a pressure threshold associated with the sensor in the treatment tracking database;
    compare the pressure threshold and the amount of pressure; and
    generate an alert if the amount of pressure is beyond the pressure threshold.

17. The system of claim 15 wherein each of the first inductive electrode and the second inductive electrode has a coiled shape.

18. An orthodontic aligner for use in orthodontic treatment comprising:

a pocket defined by the aligner and adapted to receive a portion of a tooth therein and to apply a periodontal pressure in a range that moves the tooth relative to surrounding gum tissue;

at least two inductive sensors disposed in the aligner proximate the pocket and adjacent the buccal surface or the lingual surface of the tooth, wherein the at least two inductive sensors are configured to measure a decreasing pressure value related to the applied periodontal pressure after the orthodontic aligner is placed on the at least one tooth and the at least one tooth is moved by the aligner.

19. A device for use in orthodontic treatment comprising:
an orthodontic aligner adapted to fit a set of teeth and to apply a periodontal pressure in a range that moves at least one tooth in the set of teeth relative to surrounding gum tissue; and
an inductive sensor having at least two electrodes, each electrode having a coiled shape, the inductive sensor disposed in the orthodontic aligner at a location adjacent one of a buccal surface and a lingual surface of the at least one tooth and being configured to sense a decreasing pressure value related to the applied periodontal pressure after the orthodontic aligner is placed on the at least one tooth and the at least one tooth is moved by the aligner.

20. A method of orthodontic treatment comprising:
providing an aligner adapted to fit the patient's teeth and capable of applying a periodontal pressure in a range that moves at least one tooth relative to surrounding gum tissue;
sensing, by a sensor disposed in the aligner, a decreasing pressure value related to the applied periodontal pressure between the aligner and the at least one tooth, the sensor comprising a first inductive electrode, a second inductive electrode, and a deforming layer disposed between the first inductive electrode and the second inductive electrode, wherein the deforming layer deforms relative to the periodontal pressure as the at least one tooth is moved by the aligner;
remotely actuating the sensor to provide the pressure value.

21. The method of claim 20, further comprising:
transmitting an input signal from a detection instrument to the sensor to remotely actuate the sensor; and
generating, by the sensor, an output signal in response to receiving the input signal, wherein the output signal signifies the pressure value.

22. The method of claim 21, further comprising:
resonating the first inductive electrode and the second inductive electrode with the input signal; and
generating the output signal via the resonating of the first inductive electrode and the second inductive electrode.

23. The method of claim 20, further comprising:
disposing a deforming layer between the first inductive electrode and the second inductive electrode in the sensor, wherein the first inductive electrode and the second inductive electrode in the sensor are spaced apart by a distance; and
deforming the deforming layer in proportion to a pressure exerted on the tooth to alter the distance, wherein the pressure value is based at least in part on the distance.

24. The method of claim 20, further comprising:
collecting the pressure value by a detection instrument; and
communicating the pressure value from the detection instrument to a treatment tracking software application.

25. The method of claim 24, further comprising:
displaying, by the treatment tracking software application, the pressure value on a display.

26. The method of claim 24, further comprising:
determining, by the treatment tracking software application, whether the pressure value is beyond a threshold; and
in response to determining the pressure value is beyond the threshold, notifying a treatment professional associated with the aligner.

27. The method of claim 24, further comprising:
determining, by the treatment tracking software application, whether the pressure value is beyond a threshold; and
in response to determining the pressure value is beyond the threshold, generating an alert.

28. The method of claim 27, further comprising:
communicating the alert to a treatment professional associated with the aligner via a text message or an email message.

29. The method of claim 20, further comprising:
downloading an application onto a computing device;
actuating the application to transmit an input signal from the computing device to the sensor to actuate the sensor;
generating, by the sensor, an output signal signifying the respective pressure value in response to receiving the input signal; and
collecting, by the computing device, the output signal.

30. The method of claim 29, wherein the input signal is generated by the computing device in accordance with a near field communication protocol.

31. The method of claim 30, wherein the computing device is a smartphone or a tablet computer.

32. The method of claim 29, wherein the computing device is associated with a patient undergoing treatment with the aligner.

33. The method of claim 29, further comprising:
communicating the pressure value from the computing device over the Internet to a treatment tracking software application.

34. A method of orthodontic treatment comprising:
quantifying a pressure value related to a periodontal pressure applied to each tooth in a set of teeth by an orthodontic aligner fitting over the patient's teeth and applying a periodontal pressure in a range that moves at least one of the patient's teeth relative to surrounding gum tissue, the orthodontic aligner including a sensor disposed in the orthodontic aligner and comprising a first inductive electrode, a second inductive electrode, and a deforming layer disposed between the first inductive electrode and the second inductive electrode, wherein the deforming layer deforms relative to the periodontal pressure and the sensor senses a decreasing pressure value related to the applied periodontal pressure between the aligner and the at least one tooth; and
providing the pressure value for each tooth to a treatment professional associated with the aligner.

35. The method of claim 34, further comprising:
associating a maximum pressure threshold for the at least one tooth; and
communicating an alert to the treatment professional if the quantified pressure value for the at least one tooth is above the maximum pressure threshold.

36. The method of claim 34, further comprising:
associating a minimum pressure threshold for each tooth in the set of teeth; and determining whether the quantified pressure value is below the minimum pressure threshold for each tooth in the set of teeth; and in response to determining the quantified pressure value is below the minimum pressure threshold for each tooth in the set of teeth, terminating treatment with the aligner.

* * * * *